(12) United States Patent
Lloyd et al.

(10) Patent No.: US 8,836,521 B2
(45) Date of Patent: Sep. 16, 2014

(54) HYDRATION ALERT

(75) Inventors: Duane Lloyd, Glasgow, MT (US);
Douglas E. Ott, Macon, GA (US)

(73) Assignee: Lexion Medical LLC, St. Paul, MN (US)

( * ) Notice: Subject to any disclaimer, the term of this patent is extended or adjusted under 35 U.S.C. 154(b) by 0 days.

(21) Appl. No.: 13/507,733

(22) Filed: Jul. 24, 2012

(65) Prior Publication Data

US 2013/0249697 A1    Sep. 26, 2013

Related U.S. Application Data

(63) Continuation of application No. 12/288,133, filed on Oct. 16, 2008, now Pat. No. 8,269,638.

(60) Provisional application No. 61/062,064, filed on Jan. 23, 2008.

(51) Int. Cl.
*G08B 21/00* (2006.01)
*G08B 21/18* (2006.01)
*A61M 13/00* (2006.01)
*A61M 37/00* (2006.01)
*A61M 31/00* (2006.01)
*A61B 5/08* (2006.01)
*A61M 16/16* (2006.01)
*A61M 16/10* (2006.01)

(52) U.S. Cl.
CPC ...... *G08B 21/182* (2013.01); *A61M 2205/3653* (2013.01); *A61M 2205/3331* (2013.01); *A61M 2205/18* (2013.01); *A61M 16/16* (2013.01); *A61M 16/105* (2013.01); *A61M 16/161* (2013.01); *A61M 16/109* (2013.01); *A61M 2205/50* (2013.01); *A61M 13/003* (2013.01); *A61M 2205/3368* (2013.01); *A61M 2205/3379* (2013.01)
USPC ............ 340/612; 340/603; 340/635; 604/23; 604/26; 604/65; 600/534

(58) Field of Classification Search
USPC .................. 340/612, 603, 635; 604/23, 26, 65
See application file for complete search history.

(56) References Cited

U.S. PATENT DOCUMENTS 6,632,194 B1 * 10/2003 Mehner et al. ................... 604/26
8,545,416 B1 * 10/2013 Kayyali et al. ................ 600/534
2006/0052742 A1 * 3/2006 Ott et al. .......................... 604/23

* cited by examiner

*Primary Examiner* — Jack K Wang
(74) *Attorney, Agent, or Firm* — Jacobson & Johnson LLC

(57) ABSTRACT

One aspect of the invention is an apparatus including an alarm for alerting an operator to recharge a humidifier, wherein such alarm is generated other than through the use of a humidity sensor. In one embodiment the total work performed during heating and hydrating an insufflation gas is measured and an alarm generated when the total work performed exceeds a particular threshold. In another embodiment, a flow meter is used to measure the total flow of insufflation gas so that when the total flow of insufflation gas reaches a predetermined level an alarm is activated.

13 Claims, 2 Drawing Sheets

HYDRATION ALERT

CROSS REFERENCE TO RELATED APPLICATIONS

This application is a continuation application of Ser. No. 12/288,133 filed Oct. 16, 2008 now U.S. Pat. No. 8,269,638 titled HYDRATION ALERT, which claims priority of provisional application titled Hydration Alert Ser. No. 61/062,064 filed Jan. 23, 2008.

FIELD OF THE INVENTION

This invention relates generally to medical procedures and, more specifically, to an apparatus and method for determining when to charge a hydrator in a medical insufflation apparatus.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of a medical apparatus for humidifying or otherwise treating n gas from an insufflator during surgery is described in Douglas Ott et al. U.S. Pat. Nos. 5,411,474; 6,068,609 and 7,066,902. Briefly, an insufflation gas is heated and hydrated before the gas is directed into a body cavity through a device such as a trocar. In order to hydrate the insufflation gas a charge of hydration fluid is typically injected into a chamber where the hydration fluid can humidify the insufflation gas before the insufflation gas is injected into a body cavity of a patient. Typically, a charge of hydration fluid is injected into a heater hydrator to humidify the insufflation gas as it travels through a chamber in the heater hydrator. When the charge of hydration fluid injected into the heater hydrator is spent or runs low, then a fresh charge may be introduced into the heater hydrator.

SUMMARY OF THE INVENTION

The present invention provides an alert system that may generate an alert to recharge hydration fluid in a humidifier when such a recharge is desirable such as when a charge of hydrated fluid used to hydrate insufflation gas is running low or has been consumed.

One aspect of the invention is an apparatus including an alarm for alerting an operator to recharge a humidifier, wherein such alarm is generated other than through the use of a humidity sensor. In one embodiment the total work $W_T$ (which can be calculated by integrating a function of power versus time)) performed during heating and hydrating an insufflation gas is measured to provide an alert signal. The alert signal can activate an alarm when the total work performed is more than a particular threshold. In another embodiment, a flow meter or a mass meter is used to measure the total flow of insufflation gas so that when the total flow of insufflation gas reaches a predetermined level an alarm is activated.

The invention has several important technical advantages. Embodiments of the invention may have none, some, or all of these advantages. The invention may allow more accurate determination of when a humidifier should be recharged than is possible with a humidity sensor. Because humidifiers used in medical procedures may be disposable, the methods disclosed in the present invention may be superior from a cost and waste standpoint as reusable components can be used to sense the need for recharge instead of using a disposable humidity sensor. The invention may allow multiple methods to be used simultaneously to create a signal that a humidifier should be recharged with humidifying liquid, thus providing a way to verify recharge is desirable.

DESCRIPTION OF THE PREFERRED EMBODIMENT

Figure 1:
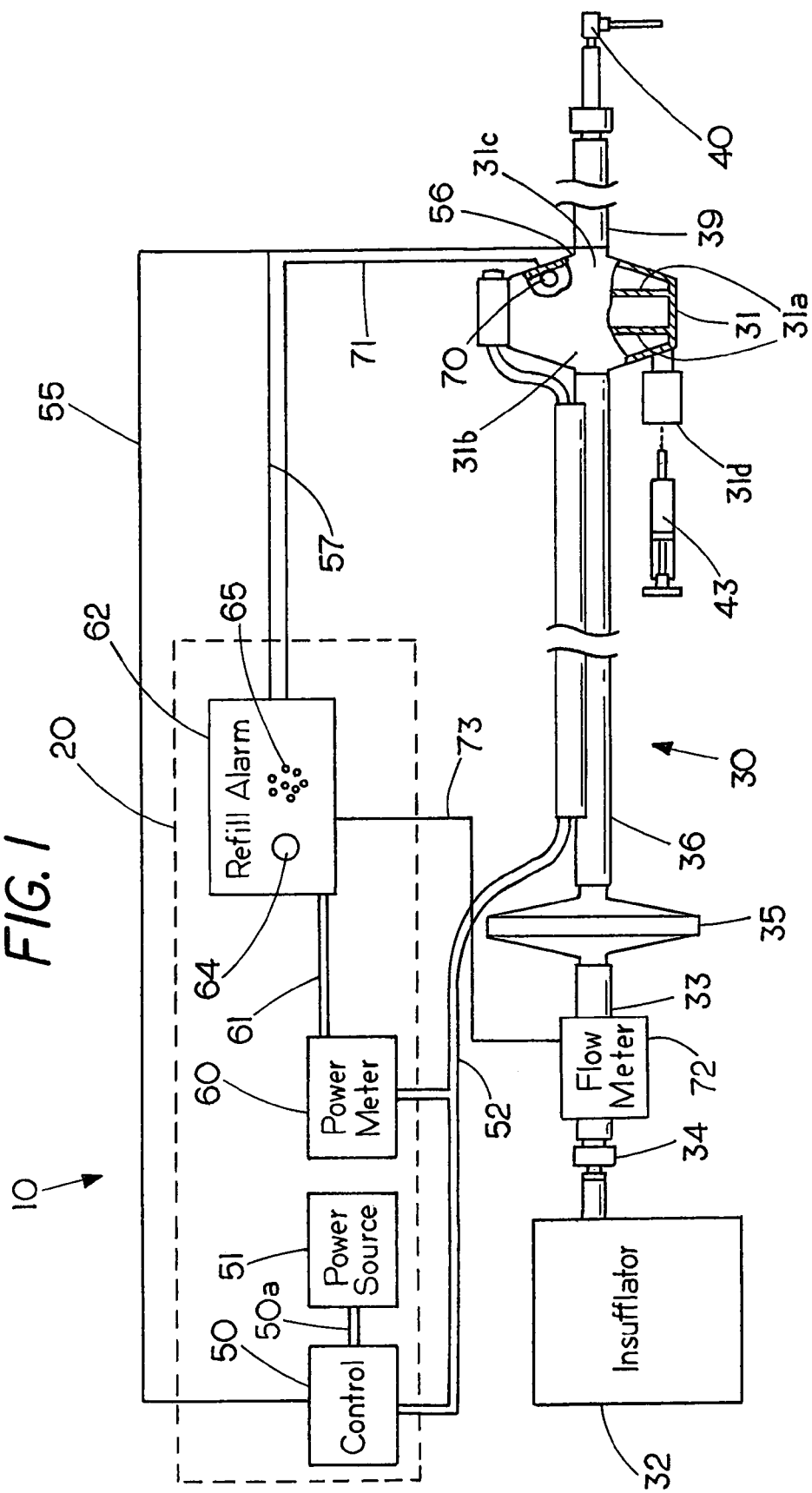
FIG. 1 is a schematic view of one embodiment of a refill system in conjunction with an apparatus for conditioning an insufflation gas.

FIG. 1 shows an apparatus 10 for maintaining conditioning of an insufflation gas during a medical procedure. Typically, the medical procedure is endoscopy and more specifically laparoscopy. The invention may also be used during thoracoscopy. The system may include a heater hydrator 31 for heating and hydrating an insufflation gas delivered from an insufflator 32 that supplies an insufflation gas to the heater hydrator as needed. In some embodiments, heater hydrator 31 may be replaced by a hydrator alone. Insufflator 32 is a laparoscopic insufflator in this embodiment.

Located within (or surrounding) heater hydrator 31 is an electrical heater 31a for heating an insufflation gas to a temperature within a desired temperature range, which typically is about 34-38° C. The insufflator 32 connects (typically indirectly) to heater hydrator 31 through, for example, a coupling 34, a flow meter 72, tubing 33 a filter 35 for removing impurities and a tubing 36 that is secured to an inlet 31b of heater hydrator 31. An outlet 31c on heater hydrator 31 may connect to tubing 39 that connects to a trocar 40 (or verres needle) for delivery of the conditioned insufflation gas to a body cavity of a patient during a medical procedure. Thus the insufflator 32 regulates the flow of insufflation gas, which is usually located in the operating room. Systems for delivery of insufflation gas are shown in Ott et al. U.S. Pat. No. 6,068, 609, which is hereby incorporated by reference. Note that in some embodiments the heater may be in tubing leading to the patient (e.g. between an insufflator and a trocar or verres needle). Some or all of these components may be omitted or rearranged without departing from the scope of the invention. For example, flow meter 72 may be omitted if the flow meter is not being used to sense when recharge is desirable. Flow meter 72 may also be a part of insufflator 32. Insufflator 32 may also have one or more flow meters in addition to flow meter 72. Flow meter 72 may be placed at any point between insufflator 32 and a patient. In some embodiments, filter 35 may be omitted or located in a different place along the flow channel. Ideally, tubing 39 is less than 24 inches long, more ideally less than 15 inches long, more ideally less than 10 inches long, and more ideally less than 6 inches long. Other lengths of tubing 39 may be used without departing from the scope of the invention. In addition, tubing could be placed between coupling 34 on insufflator 32 and flow meter 72. These are only a few examples of how components could be rearranged, added, or omitted, without departing from the scope of the invention.

In operation of system 10 a valve (not shown) on a trocar 40 or the like is opened to allow the insufflation gas to flow from insufflator 32 through coupling 34, a flow meter 72, tubing 33, a filter 35 and tubing 36 whereupon it enters heater hydrator 31. A control 50 may comprise, for example, a microcontroller or other electric circuitry to regulate the power delivered to heater 31a from a power source 51. The insufflation gas enters the heater hydrator 31 and is heated by the heater 31a to a temperature within a desired temperature range. In a preferred embodiment the control 50 comprises a microcontroller with pulse-width modulation outputs. A conventional power mosfet can be connected to the microcontroller pulse-width modulation outputs to turn the power on and off to the heater 31a. Analog circuits may also be used to control power such as are described in U.S. Pat. No. 5,411,474. As will be discussed further below, control 50 may be external to or internal to Insufflator 32.

In addition to heating the insufflation gas to the proper body entry temperature in embodiments where gas is heated, the insufflating gas may also be hydrated by the presence of a charge of hydration fluid in heater hydrator 31. Humidification may occur in any manner such as by gas flowing through and/or over the hydration fluid or by flowing through and/or over an absorbent material that has absorbed some or all of the hydration fluid.

Because hydration fluid is consumed during an operation, it is desirable to replenish it from time to time during at least some operations. The insufflation gas is typically supplied from a pressurized cylinder of insufflation gas (not shown) within or connected to insufflator 32. A supply of gas from another source such as one might find supplied from the wall of an operating room from a centralized supply may also be used. As gas leaks out or is deliberately released from a patient's abdomen during a laparoscopic procedure, insufflator 32 may control the flow of gas such that the released gas is replenished. Insufflator 32 may also provide flow control to control the maximum flow rate of gas from the insufflator to the patient and pressure control to control the maximum pressure at which insufflator 32 provides gas to the patient. In most insufflators 32, the maximum pressure and flow rate are adjustable by the user of the apparatus. Depending upon the amount of gas consumed during a surgical procedure, the humidifier may or may not require recharging with humidifying liquid.

In operation of the system 10 the insufflation gas is hydrated by the consumption of hydration fluid in the heater hydrator 31. Hydration fluid may be supplied to heater hydrator 31 by various means. In the embodiment shown one can use a syringe 43 to manually inject a charge of hydration fluid into the heater hydrator 31 through a charging port 31d. One can charge or recharge (or both) heater hydrator 31 in this manner. Other modes could include automatic injecting of a hydration fluid into the heater hydrator through a dedicated hydration fluid supply line connected to heater hydrator 31. Whatever method is used, a quantity (which quantity may be known approximately) of hydration fluid may be introduced in some manner into the heater hydrator, which is designated herein as a charge of hydration fluid. While the hydration fluid is injected into the heater hydrator 31 through a charging port 31d in this embodiment, other methods of replenishing the hydration fluid can be used. For example, fluid could be introduced through the gas inlet or outlet of heater hydrator 31.

Hydration fluid can be any desirable hydration fluid such as, for example, water, saline solution, or distilled water. In other embodiments, hydration fluid may include a drug such as an anesthetic, antibiotic, etc.

In various embodiments of the invention, the user is alerted as to when to recharge the heater hydrator 31 through the use of a refill alarm system 20, shown in FIG. 1 in dashed lines. To heat the insufflation gas, a power source 51 may supply power through electrical leads 52 to the heater 31a. The heater may heat both the insufflation gas and the hydration fluid to be within a desirable temperature range for provision of the heated and humidified insufflation gas into a body cavity. In the embodiment shown, a temperature sensor 56 within the heater hydrator 31 connects to control 50 through wire lead 55 for use in determining whether the heated and humidified gas is within the proper temperature range. The microcontroller in control 50 (or suitable analog circuitry) may turn on (or pulse) the mosfet in control 50 allowing the power source 51 to supply power to the heater 31a through electrical leads 52. Other methods of power control can also be used without departing from the scope of the invention. Thus, the insufflating gas can be maintained within the proper temperature range through the use of heater 31a, temperature sensor 56 and control 50.

In some embodiments, multiple temperature sensors 56 may be used. For example, two temperature sensors could be used and a malfunction detected if their measured temperature varied more than a predetermined amount. In some embodiments, heater hydrator 31 will have a fixed temperature range that is not adjustable. In other embodiments, controls may be provided to adjust the temperature range. Also, temperature sensor 56 may be placed anywhere within heater hydrator 31 or external to heater hydrator 31. More responsive temperature control can normally be obtained if temperature sensor 56 is sensing a temperature equal to or proportional to the temperature of the gas after it has been heated and humidified. Also, temperature sensor 56 could be located in tubing 39 or in trocar 40.

Work done by the heater 31a to maintain the insufflation gas in a hydrated condition within a desirable temperature range may be proportional to the quantity of hydration fluid consumed. By measuring the work performed by the heater 31a during the heating and hydration process, one can determine when it may be desirable to replenish the hydration fluid. One can measure the work performed when heating and hydrating an insufflation gas when using a full charge or near full charge of hydration fluid. In other words, one can charge the device and then heat and hydrate a sufficient quantity of gas to deplete (either completely or substantially) the hydration fluid. One can experimentally determine the work performed in depleting the hydration fluid. By such measurement, one can obtain a total work level $W_T$. Once the total work level $W_T$ is known, one can then experimentally determine a recharge work level $W_C$, which is equal to or less than the total work $W_T$, to use for activating the alarm to alert a person to recharge the heater hydrator 31. For example, one can select a work amount of $0.9 W_T$ as a work level where an alarm is sounded to indicate that the heater hydrator 31 should be recharged.

Work can be measured by making a series of power measurements using power sensors or current and voltage sensors. In some embodiments, a power meter may be used to make a series of power measurements. Where a microcontroller is used, the voltage supplied to the heater may be known and a current sensor may be used to measure the current that is then multiplied by the known voltage to determine instantaneous power. Work can be calculated by determining the area under a graph of power versus time. Most often, some type of numerical method will be used to calculate work such as, for example, (a) assuming a power measurement is constant for a particular amount of time, or (b) by using some type of interpolation using multiple power measurements. Thus, a series of power measurements can be made and the total work performed during a period of time calculated using the power measurements and time. For purposes of this application, any calculation that approximates work will be considered to be a measurement of work. The accuracy of a particular recharge signal may depend upon the accuracy of the measurement of work (both during operation of the device and in the initial experiments to determine the total work performed while a charge is evaporating).

The time of consumption of a charge of hydration fluid cannot be reliably predicted because the amount of insufflation gas consumed and hence the amount of hydration fluid consumed during a particular time period can vary greatly depending upon the surgical procedure. However, when sufficient hydration fluid has been consumed that the gas is not reaching approximate saturation, the power consumption of the heater hydrator 31 will decline because less heat is consumed by the humidification process. By measuring the total work performed, one can indirectly determine that the humidity of the humidified gas is declining. The invention thus advantageously allows recharging of the hydration fluid in many instances before complete consumption of the hydration fluid has occurred.

In order to perform the power measurements described above, control 50 may include an internal power sensor in the microcontroller (or other analog circuitry to sense power) or an external power sensor 60. Control 50 (or suitable analog or digital circuitry) may be programmed with the work levels $W_T$ and $W_c$. Control 50 may then activate an alarm when the total work performed exceeds the $W_c$ level. In some embodiments, due to tolerances of electrical components, control 50 may adjust $W_T$ and $W_c$ based upon power levels measured during operation of the device. In some embodiments, a temperature sensor may be provided at the inlet of the device to measure the inlet temperature of the gas entering the heater/humidifier 31. The inlet temperature may be used to adjust the values of $W_T$ and $W_c$ to provide proper control.

In order to supply power to the heater 31a either an analog or digital power supply can be used. In this embodiment, control 50 may control the power delivered to the heater hydrator 31a using pulse-width modulation as discussed above. Suitable microcontrollers for providing pulse-width modulation are commercially available from numerous sources including Microchip Technology, Inc. of Chandler Ariz.

Refill alarm system 20 may include a meter (not explicitly shown) that measures the total work performed by power source 51. Typically, a work meter such as a watt-hour meter can be used to measure the total work if pulse-width modulation is not used. When the total work performed reaches a preset level $W_C$, a signal may be sent to a refill alarm 62 though electrical leads 61. The refill alarm 62 can include a visual alarm 64 such as a light or LED and/or an audible alarm 65 such as a bell or a buzzer. Still other types of devices are useable with the invention including electronic or vibratory devices.

In other embodiments, it is possible to establish a range of instantaneous power that indicates normal operation. As the charge of hydration fluid is exhausted, less power will be required to heat the gas. Thus, it is possible in some embodiments to establish a threshold below which the instantaneous power should not drop over a sustained period of time when insufflation gas is flowing. This method needs to take into account that gas may be flowing rapidly or not at all during a typical surgery. Thus, gas flow should preferably be taken into account when using this method. One could use the flow meter 72 or flow meters within insufflator 32 (or signals therefrom indicating flow) to determine the flow rate of the insufflation gas. One could determine that hydration fluid needs to be recharged by determining whether the instantaneous power drops below a threshold either once or multiple times over a specific time period. Such a threshold could be different for different flow rates or ranges of flow rates.

It should be noted that in some systems, there will be time periods where no power is being supplied to the heater in heater hydrator 31. Control 50 may be designed such that it does not perform comparisons of power consumption during those time periods. In addition, there will be time periods where little or no insufflation gas is flowing and less power will be needed to maintain the temperature and humidity of the gas within heater/hydrator 31. In an embodiment where the instantaneous power level triggers the alarm, the threshold power level should be chosen to be low enough (or other control exercised such as not making a comparison during no-flow or low-flow conditions) such that no-flow or low-flow conditions do not trigger the alarm.

Figure 2:
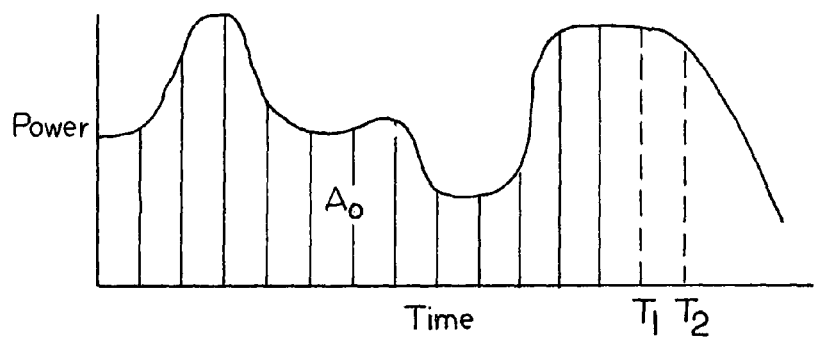
FIG. 2 is an example graph of the power consumed as a function of time during a medical procedure.
Figure 3:
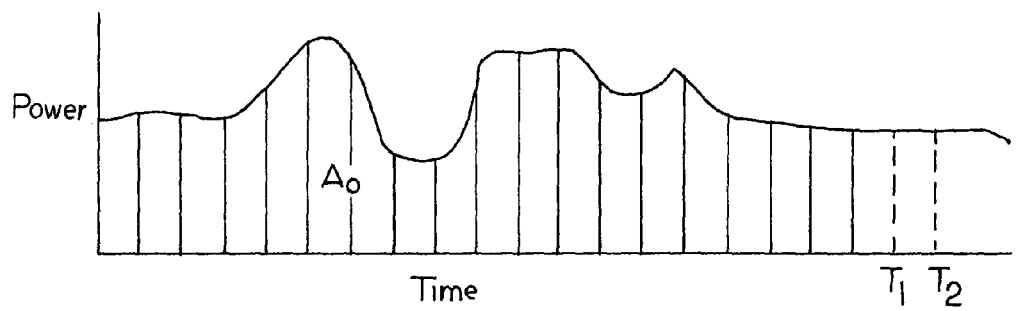
FIG. 3 is an example graph of the power consumed as a function of time during a different medical procedure.

FIG. 2 is a graph illustrating how power may vary verses time during an example laparoscopic surgery. In the graph, the area $A_o$ under the curve represents the total work and the horizontal axis represents the time elapsed. At a time $T_2$ the power needed to heat the insufflation gas and the hydration fluid to the proper conditions state drops off rapidly due to the consumption of the initial charge of hydration fluid in the heater hydrator. FIG. 3 shows a similar graph of power versus time during another example medical procedure. Note that the labels T1 and T2 are unique to each of FIGS. 2-4 and do not represent the same time in the different figures. In other words, these Figures are independent of one another and the use of the same labels does not indicate the same time. The same is true of A0, the area under the curve. This area is different for each of FIGS. 3-4.

Figure 4:
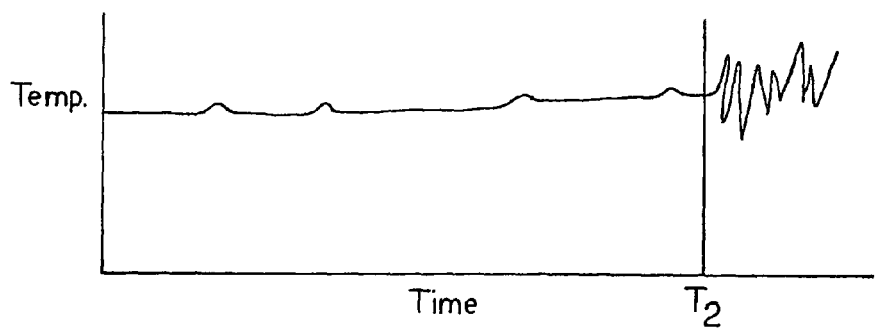
FIG. 4 is an example graph of temperature of the hydration fluid as a function of time.

FIG. 4 shows a graph of a temperature signal of the insufflation gas in the heater hydrator 31 as a function of time as measured by temperature sensor 56. The output generally is constant with minor variation as hydration fluid is consumed in the hydrator. Once hydration fluid in the heater hydrator 31 is totally consumed at time $T_{2'}$, however, the measured temperature may change more erratically in some embodiments. The change in the pattern of the temperature sensor signal can be used to confirm that the hydration fluid in the heater hydrator 31 has been consumed.

The change in temperature signal can be used as a confirmation that the hydration fluid has been consumed in hydrating the insufflation gas. An alarm can be generated when this occurs or the power shut down to the heater or both. Thus, an additional feature of the invention can include the monitoring of the temperature signal of the conditioned gas proximate or inside the heater hydrator and activating an alarm when the temperature signal of the insufflation gas begins to vary significantly as illustrated in FIG. 4.

A reference to system 10 in FIG. 1 shows an optional humidity sensor 70 located in heater hydrator 31 with the humidity sensor 70 sending information on the humidity of the insufflation gas to refill alarm through lead 57. If the output of the humidity sensor 70 decreases below an acceptable level the refill alarm 62 may alert an operator to the low hydration condition through an alarm using either an audio alarm 65 or a visual alarm 64 or both. Humidity sensors sold by Ohmis Instruments Co. of Easton Md. and America Humirel of Chandler Ariz., for example, may be used.

In some embodiments, humidity sensor 70 will be omitted. In some embodiments, multiple humidity sensors will be used in the manner that multiple temperature sensors were used above. In other embodiments, one or more humidity sensors 70 may be used in conjunction with any of the other techniques discussed herein to indicate when a recharge of humidification liquid is desirable. For example, a recharge may not be indicated by an alarm until multiple methods indicate that a recharge is desirable. It should be noted that any of the methods discussed herein can be used to turn off the heater in heater hydrator 31 in addition to or instead of providing an alarm.

The total amount of insufflation gas supplied to the heater hydrator 31 may be proportional to the consumption of hydration fluid. By measuring the total quantity or volume of insufflation gas supplied to the heater hydrator 31 during the heating and hydration process, one can provide an indication of when to replenish the hydration fluid. One can experimentally determine the total volume of insufflation gas supplied to the heater hydrator 31 that exhausts (or substantially exhausts) a predetermined quantity of hydration fluid to obtain a total flow level $Q_T$. Experiments will show a small range of total flow and the minimum value of total flow that substantially exhausts the hydration fluid would preferably be chosen as the value to test against. Once $Q_T$ is known one can then determine a recharge total flow $Q_C$, which is equal or less than the total flow $Q_T$, to use for activating the alarm to alert a person to recharge the heater hydrator 31 before the hydration fluid is consumed. For example, one can select a total gas flow of 0.9 $Q_T$ as a total gas flow where the user should be alerted to recharge the heater/hydrator 31 with fluid. By measuring the total volume of insufflation gas consumed, one can indirectly determine a desirable time to replenish the hydration fluid in the heater hydrator without measuring humidity.

FIG. 1 also shows a sensing system for measuring the total volume of insufflation gas consumed comprising a flow meter 72 that measures the total volume of insufflation gas that flows therethrough. The total flow of insufflation gas can be monitored by flow meter 72 to send a signal to refill alarm 62 or to control 50 which may control refill alarm 62. Note that refill alarm 62 may be controlled by control 50 in any embodiment. For example, once the total flow reaches a level $Q_1$ the refill alarm 62 provides either an audio or visible alarm to alert the operator to recharge the heater hydrator 31. Flow meters for measuring total flow are commercially available from Motorola of Schaumburg Ill. Another commercially available Airflow and Temperature sensor is sold by One Technology of Norwood Mass. There are many possibilities for using one or more of these methods to determine when to recharge a heater hydrator. The measurements of flow of insufflation gas, instantaneous power, temperature, or work in heating and hydrating can be used alone or in combination. If used in combination one can serve as a backup for the other. For example, the flow meter 72 could provide the first indicator of low humidity thereby activating the visible alarm 64 and the power consumed could provide the second alarm alerting the operator by activating the audible alarm. Either method alone could activate either alarm. Also, both might need to indicate a recharge condition before any alarm was activated. Thus the invention includes circuitry responsive to a sensor for determining when a heater humidifier used with a laparoscopic insufflator should be recharged with humidifying liquid in response to a signal from a sensor by providing an alert signal, which can activate an alarm.

Although refill alarm system 20 is shown as separate from insufflator 32, some or all of the circuitry could be a part of insufflator 32. Refill alarm system 20 could be separate control circuitry within insufflator 32 or could be integrated in whole or in part with the control circuitry of insufflator 32. As insufflator 32 typically includes one or more flow meters 72 and keeps track of the total volume of gas consumed, refill alarm system 20 could be provided with electrical signals from a flow meter inside of insufflator 32 or that provide the total volume of gas supplied by insufflator 32 during a procedure. While a flow meter is described to measure the volume of gas consumed and provide an electrical signal one could also measure the mass or quantity of gas consumed with a mass meter to provide a signal to the control circuitry.

We claim:

1. An alert system for use during a medical procedure for replenishing a hydration fluid in a heater hydrator without measuring the humidity comprising:
    an insufflator for supplying an insufflation gas to a hydrator;
    a first sensor comprising a flow meter for providing a first signal responsive to a flow of insufflation gas wherein the first signal is proportional to the consumption of the hydration fluid; and
    a circuitry responsive to the first sensor for determining when the heater hydrator should be recharged with the humidifying fluid in response to the first signal wherein the first signal is less than a second signal that has been determined experimentally to indicate the flow of insufflation gas has exhausted the hydration fluid in the heater hydrator.

2. The alert system of claim 1, further comprising:
    an alarm responsive to an alert signal from the circuitry wherein the alarm is activated when a recharge determination is made by the circuitry.

3. The alert system of claim 1, further comprising:
    a further sensor for providing a third signal that may be used to estimate at least one of instantaneous power consumption of a heater or work done by a heater; and
    wherein the circuitry makes the recharge determination in response to the first signal from the first sensor and the third signal from the further sensor.

4. The alert system of claim 3 wherein the further sensor comprises either a current sensor, a voltage sensor, or a work sensor.

5. The alert system of claim 1 including a temperature sensor wherein an alarm is activated when a temperature signal from the temperature sensor changes during a time period and both exceeds a high threshold and drops below a low threshold during that time period.

6. A method to determine when to recharge a heater hydrator comprising:
    supplying an insufflation gas to a heater hydrator from a laparoscopic insufflator comprising a heater;
    determining a total flow of insufflation gas that exhausts the hydration fluid in the heater hydrator;
    measuring a total volume of insufflation gas supplied to the heater hydrator; and
    activating an alarm when the flow of insufflation gas is equal to or less than the total flow of the insufflation gas that would exhaust the hydration fluid in the heater hydrator.

7. The method of claim 6 further comprising:
    recharging the heater hydrator before all of the hydration fluid contained therein has been consumed.

8. The method of claim 6 wherein the step of activating an alarm comprises activating a visual alarm.

9. The method of claim 6 wherein the step of activating an alarm comprises activating an audible alarm.

10. The method of claim 6 further comprising monitoring the temperature proximate an exit of the heater hydrator and disabling the heater when the temperature changes in a way over time such that it both exceeds a high temperature threshold and drops below a low temperature threshold during a time period.

11. The method of claim 6, further comprising disabling the heater after the instantaneous electrical power supplied to the heater falls below a particular threshold when power is being supplied to the heater and when gas is flowing through the heater hydrator.

12. The method of claim 6 including the step of monitoring the temperature of the insufflation gas after it has been humidified by the heater hydrator.

13. The method of claim 6, further comprising recharging the heater hydrator in response to the alarm.

\* \* \* \* \*